United States Patent [19]

Nozomi et al.

[11] Patent Number: 5,037,714
[45] Date of Patent: Aug. 6, 1991

[54] ELECTROPHOTOGRAPHIC PHOTORECEPTOR

[75] Inventors: Mamoru Nozomi, Yokohama; Hiromi Horiuchi, Tokyo; Sumiko Watabe, Yokohama, all of Japan

[73] Assignee: Mitsubishi Kasei Corporation, Tokyo, Japan

[21] Appl. No.: 554,296

[22] Filed: Jul. 17, 1990

[30] Foreign Application Priority Data

Jul. 18, 1989 [JP] Japan ................................. 1-185074

[51] Int. Cl.⁵ .................................................. G03G 5/14
[52] U.S. Cl. ........................................................ 430/58
[58] Field of Search ............................................ 430/58

[56] References Cited

U.S. PATENT DOCUMENTS 3,652,268  3/1972  Rowe .................... 430/55
4,407,919  10/1983  Murayama et al. ......... 430/58

Primary Examiner—David Welsh
Attorney, Agent, or Firm—David G. Conlin; Gregory D. Williams

[57] ABSTRACT

Disclosed herein is an electrophotographic photoreceptor having on a conductive base at least one charge generation layer and at least one charge transfer layer, which comprises a sulfonate ester compound represented by the general formula (I):

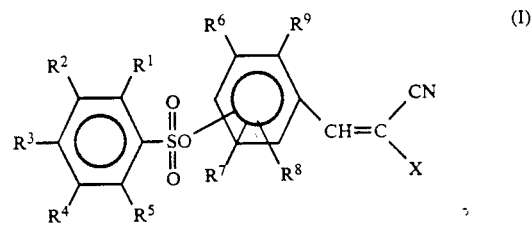

wherein $R^1$, $R^2$, $R^3$, $R^4$ and $R^5$ are independently hydrogen atom, halogen atom, cyano group, nitro group or alkyl group; $R^6$, $R^7$, $R^8$ and $R^9$ are independently hydrogen atom or halogen atom; and X is cyano group, alkoxycarbonyl group, optionally substituted aryloxycarbonyl group or optionally substituted aryl group, in the charge transfer layer. The electrophotographic photoreceptor according to the present invention has the excellent durability.

17 Claims, No Drawings

ELECTROPHOTOGRAPHIC PHOTORECEPTOR

FIELD OF THE INVENTION

The present invention relates to an electrophotographic photoreceptor. More particularly, it relates to the electrophotographic photoreceptor having an excellent durability.

BACKGROUND OF THE INVENTION

In recent years, the electrophotography has been applied to copying machines as well as various printers since they can give images with high qualities without delay. As an photoreceptor which plays an important role in the electrophotography, the photoreceptor comprising an inorganic photoconductive material such as selenium, arsenic-selenium alloy, cadmium sulfide, zinc oxide and the like has been used. More recently, the photoreceptor comprising an organic photoconductive material was proposed. The latter has the advantages which is not a pollutant and which has a film-formability and a shapability.

As one of the organic photoreceptors, the so-called "laminated-type photoreceptor" in which a charge generation layer and a charge transfer layer are successively laminated was developed. The laminated-type photoreceptor is increasingly interested in and is expected to be widely used in the near future because it has the following advantages:

(1) the photoreceptor having high sensitivity can be obtained by suitably selecting and combining the charge generation material and the charge transfer material;

(2) the photoreceptor having high safety can be obtained because the charge generation material and the charge transfer material can be selected from a wide range of the materials; and (3) the photoreceptor can be prepared by simple coating and thus it can be prepared with low costs.

However, the prior laminated-type photoreceptors cause the electric problems such as the lowering of the charged potential, the accumulation of the residual potential and the change in the sensitivity by their repeated use. The problem as to the accumulation of the residual potential is especially serious because if the residual potential is accumulated, much copies could not be obtained. Such an accumulation of the residual potential is considered to arise from some causes, among which impurities present in the charge transfer layer are important. That is, impurities trap carriers so as to produce unmovable space charges which remain as the residual charges in the charge transfer layer. The increase of the thickness of the charge transfer layer is effective for reducing the effects of the thinning down of the charge transfer layer caused by the abrasion such as blade cleaning on the electric properties and increasing the sensitivity of the photoreceptor, but it is accompanied with the increase of the amounts of impurities so that the accumulation of the residual potential makes more remarkable.

For preventing the accumulation of the residual potential caused by the impurities present in the charge transfer layer, an addition of an electron attractive compound in the charge transfer layer is attempted. Generally the addition of the electron attractive compound in the electron donative compound forms a charge transfer complex and as the result a new absorption band appears in the long wavelength region. Thus, it is considered that the accumulation of the residual potential could be prevented by irradiating the light having the wavelength which corresponds to the absorption band of the charge transfer complex to the photoreceptor so as to form a few movable carriers in the charge transfer layer, which carriers neutralize the unmovable space charges. The known electron attractive compounds are not satisfactory for preventing the accumulation of the residual potential. Further they have another disadvantages such as the increase in the dark decay, the lowering in the surface voltage and the lowering in the sensitivity by the repeated use.

The present inventors have been investigated the electron attractive compounds which can prevent the accumulation of the residual potential without affecting the other electric properties and now they found that specific sulfonate ester compounds satisfy the above requirements.

SUMMARY OF THE INVENTION

According to the present invention, an electrophotographic photoreceptor has on a conductive base at least one charge generation layer and at least one charge transfer layer, the charge transfer layer comprising the sulfonate ester compound represented by the following general formula (I).

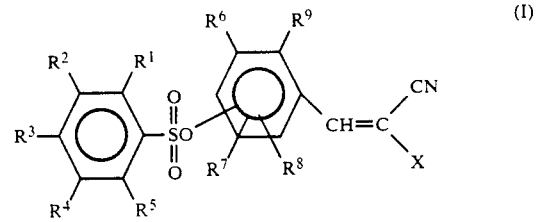

wherein $R^1$, $R^2$, $R^3$, $R^4$ and $R^5$ are independently hydrogen atom, halogen atom, cyano group, nitro group or alkyl group; $R^6$, $R^7$, $R^8$ and $R^9$ are independently hydrogen atom or halogen atom; and X is cyano group, alkoxycarbonyl group, optionally substituted aryloxycarbonyl group or optionally substituted aryl group.

DETAILED EXPLANATION OF THE INVENTION

The photoreceptor according to the present invention has the conductive base, on which the photosensitive layer comprising the charge generation layer and the charge transfer layer is provided. As the conductive base, any of the known conductive bases usually used in the electrophotographic photoreceptor can be used. Examples of the conductive base include a base made of a metallic material such as aluminium, stainless steel, copper and nickel and a base made of an insulating material such as polyester film or paper which has a conductive layer such as aluminium, copper, palladium, tin oxide and indium oxide.

A known barrier layer may be provided between the conductive base and the charge generation layer, as generally used in the photoreceptor. As the barrier layer, a layer of an inorganic material such as aluminium anodic oxide film, aluminium oxide and aluminium hydroxide or a layer of an organic material such as polyvinyl alcohol, casein, polyvinyl pyrrolidone, polyacrylic acid, celluloses, gelatin, starch, polyurethane, polyimide and polyamide is used.

The charge generation layer comprises a charge generation material and a binder resin. As the charge generation material used in the charge generation layer, various inorganic photoconductive materials such as selenium, arsenic-selenium alloy, cadmium sulfide and zinc oxide or various organic pigment or dye such as phthalocyanine, azo, quinacridone, polycyclic quinone, pyrylium salt, thiapyrylium salt, indigo, thioindigo, anthoanthrone, pyranthrone and cyanine can be used. Among them, phthalocyanine without metal, phthalocyanines coordinated with metal or its compound such as copper, indium chloride, gallium chloride, tin, oxythitanium, zinc and vanadium, azo pigments such as monoazo, bisazo, trisazo and polyazo are preferable.

As the binder used together with the charge generation material in the charge generation layer, any of the binder resins such as polyester resin, polyvinyl acetate, polyacrylate, polymethacrylate, polyester, polycarbonate, polyvinyl acetoacetal, polyvinyl propional, polyvinyl butyral, phenoxy resin, epoxy resin, urethane resin, cellulose ester and cellulose ether.

The charge generation material is used in an amount of 30 to 500 parts by weight per 100 parts by weight of the binder resin.

If necessary, the charge generation layer may contain various additives such as a leveling agent, an antioxidant and sensitizer.

The thickness of the charge generation layer is generally 0.1 to 2 μm, preferably 0.15 to 0.8 μm.

The charge transfer layer comprises the specific sulfonate ester compound, a charge transfer material and a binder resin. The sulfonate ester compound used in the charge transfer layer is represented by the general formula (I).

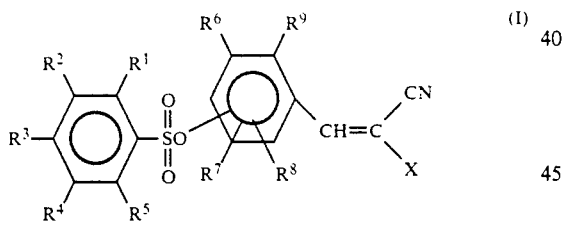

wherein $R^1$, $R^2$, $R^3$, $R^4$ and $R^5$ are independently hydrogen atom; halogen atom such as chlorine, bromine and iodine; cyano group; nitro group; or alkyl group such as methyl, ethyl and propyl. $R^6$, $R^7$, $R^8$ and $R^9$ are independently hydrogen atom or halogen atom such as chlorine, bromine and iodine. X is cyano group; alkoxycarbonyl group such as methoxycarbonyl ethoxycarbonyl, propoxycarbonyl and butoxycarbonyl; optionally substituted aryloxycarbonyl group such as optionally substituted phenoxycarbonyl and naphthoxycarbonyl; or optionally substituted aryl group such as optionally substituted phenyl and naphthyl. As the substituents on the aryloxycarbonyl group and the aryl group, one or more cyano groups, nitro groups, alkyl groups such as methyl and ethyl and halogen atoms such as chlorine, bromine and iodine are mentioned.

The sulfonate ester compound (I) can be easily synthesized, for example, by condensing a hydroxybenzaldehyde represented by the general formula (II):

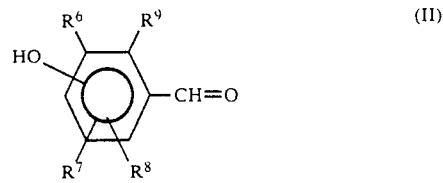

with a nitrile compound represented by the general formula (III):

followed by reacting with a sulfonyl chloride represented by the general formula (IV).

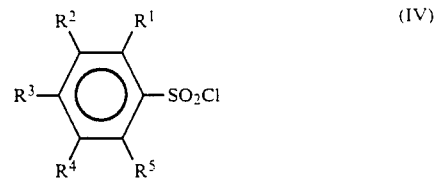

$R^1$ to $R^9$ and X in the general formulae (II), (III) and (IV) are as defined in the above.

The representative sulfonate ester compounds represented by the general formula (I are exemplified below.

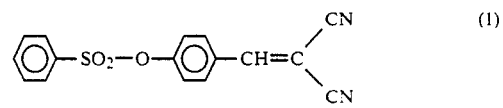

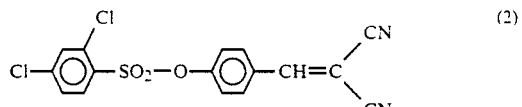

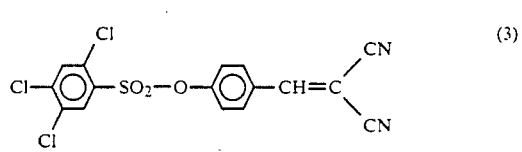

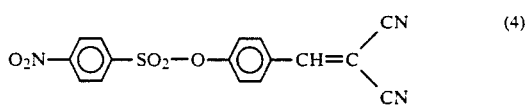

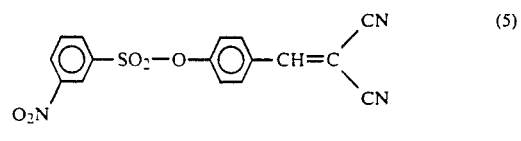

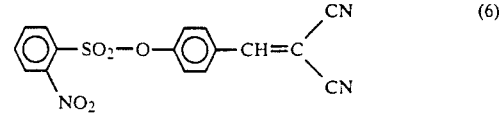

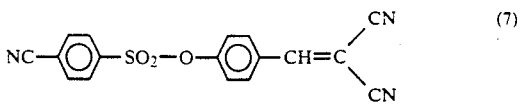

-continued
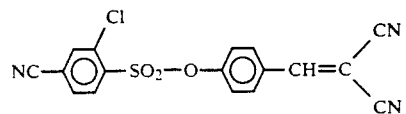 (8)
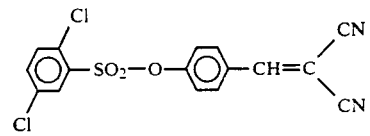 (9)
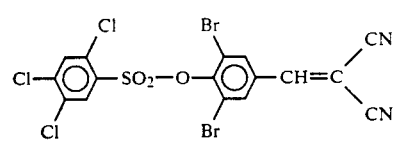 (10)
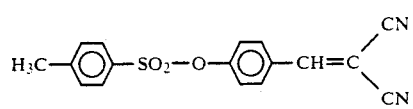 (11)
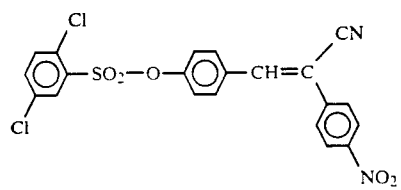 (12)
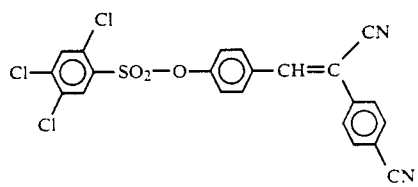 (13)
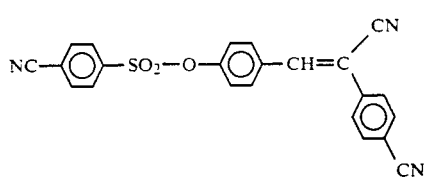 (14)
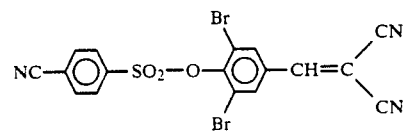 (15)
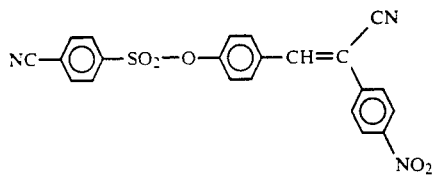 (16)
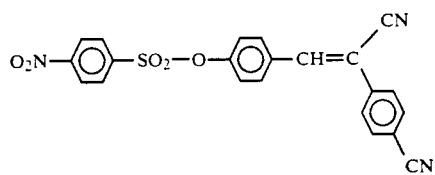 (17)
-continued
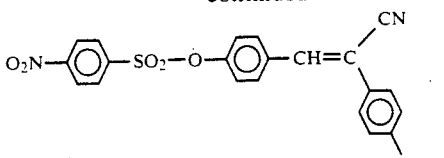 (18)
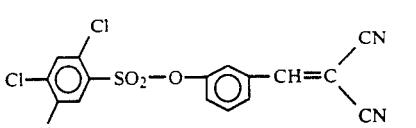 (19)
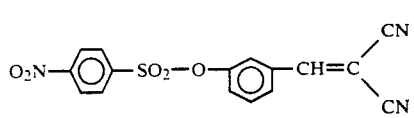 (20)
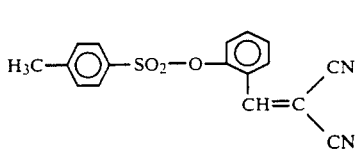 (21)
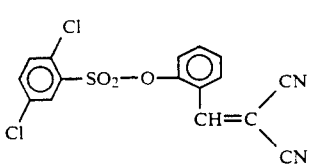 (22)
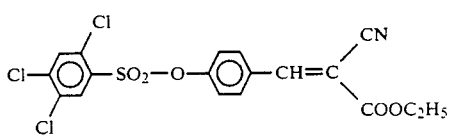 (23)
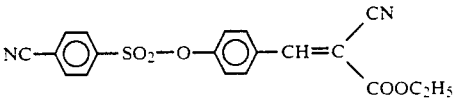 (24)
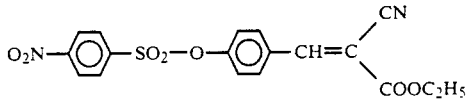 (25)
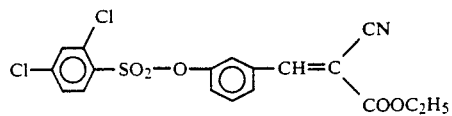 (26)
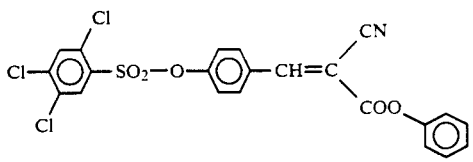 (27)
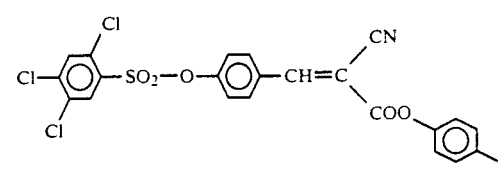 (28)

-continued

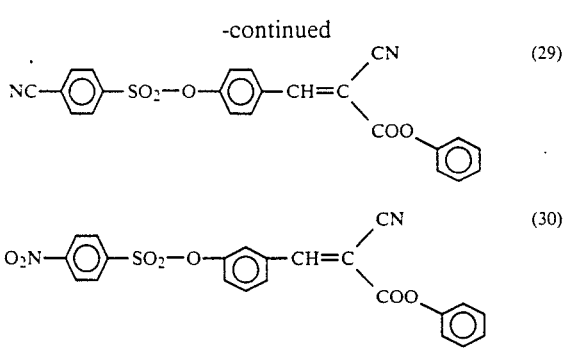

The charge transfer material used together with the sulfonate ester compound (I) in the charge transfer layer is an electron donative material, the examples of which include heterocyclic compounds such as carbazole, indole, imidazole, oxazole, pyrazole, oxadiazole, pyrazoline and thiadiazole, aniline derivatives, hydrazone compounds, aromatic amine derivatives, stilbene derivatives and polymers having the above compound in the main chain or the side chain.

As the binder resin used together with the sulfonate ester compound (I) and the charge transfer material in the charge transfer layer, a vinyl polymer such as polymethyl methacrylate, polystyrene and polyvinyl chloride and its copolymer, polycarbonate, polyester, polyester carbonate, polysulfone, polyimide, phenoxy, epoxy and silicone resins can be used. Their partially crosslinked products may be used.

The sulfonate ester compound z(I) is generally used in an amount of 0.01 to 30 parts by weight, preferably 0.1 to 10 parts by weight per 100 parts by weight of the binder resin. The charge transfer material is generally used in an amount of 30 to 200 parts by weight, preferably 40 to 120 parts by weight per 100 parts by weight of the binder resin.

If necessary, the charge transfer layer may contain various additives such as an antioxidant and a sensitizer.

The thickness of the charge transfer layer is generally 10 to 60 μm, preferably 10 to 45 μm.

EFFECT OF THE INVENTION

The electrophotographic photoreceptor comprising the specific sulfonate ester compound (I) in the charge transfer layer according to the present invention hardly shows the accumulation of the residual potential and is excellent in the charge-ability and the change in the sensitivity, even if used repeatedly.

EXAMPLES

The invention will be better understood by reference to certain examples, which are included herein for purposes of illustration only and are not intended to limit the invention.

SYNTHESIS EXAMPLE (COMPOUND NO. 3)

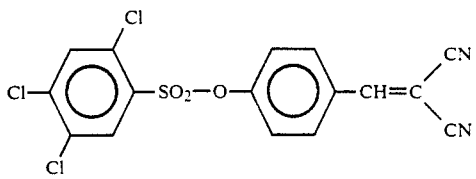

3.7 g of p-hydroxybenzaldehyde and 2.3 g of malononitrile were dissolved in 10 ml of isopropanol followed by adding 1 drop of piperidine and reacted at 80° C. for 1 hour. Crystals were precipitated after cooling to the room temperature, collected by filtration and recrystallized from isopropanol to obtain 3.6 g of 4-(2,2'-dicyanovinyl)phenol as yellow crystals. Melting point = 188–189.5° C.

1.7 g of 4-(2,2'-dicyanovinyl)phenol and 2.7 g of 2,4,5-trichlorobenzenesulfonyl chloride were dissolved in 10 ml of pyridine and reacted at 80° C. for 30 minutes. Crystals were precipitated by cooling to the room temperature and adding water, filtered and recrystallized from toluene to obtain 3.5 g of 4-(2,2'-dicyanovinyl)phenyl 2,4,5-trichlorobenzenesulfonate as white crystals. Melting point = 165–166° C.

EXAMPLE 1

10 parts by weight of a bisazo compound having the following formula:

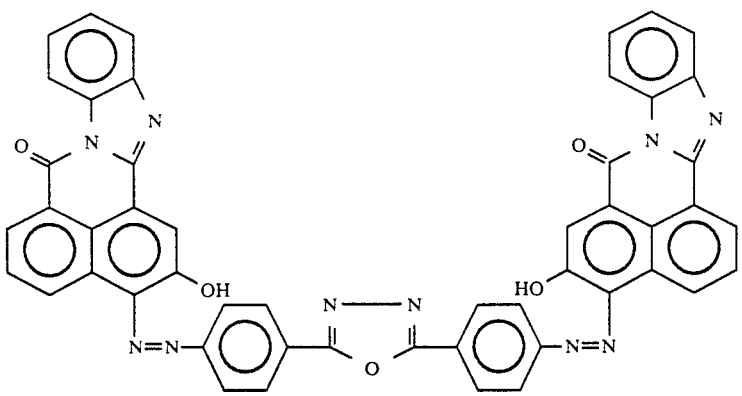

was added to 150 parts by weight of 4-methoxy-4-methylpentanone-2 and they were subjected to the grinding and dispersion treatment with a sand grind mill. The thus obtained dispersion was added to 200 parts by weight of a 5% solution of 1,2-dimethoxyethane in polyvinyl butyral (#6000-C (trade name), ex DENKI KAGAKU KOGYO KABUSHIKI KAISHA) so as to prepare a dispersion with a solid concentration of 4.0%.

In the above dispersion, an aluminium cylinder having a mirror finished surface and having the outer diameter of 80 mm, the length of 340 mm and the thickness of 1.0 mm was immersed and a charge generation layer was coated on the aluminium cylinder to provide a dried film of 0.5 μm in thickness.

This aluminium cylinder was immersed in a solution of 95 parts by weight of a hydrazone compound having the following formula:

TABLE 1

| Example | Compound No. | initial dark potential | initial residual poten. | after 300,000 times dark potential | after 300,000 times residual poten. |
|---|---|---|---|---|---|
| 1 | 3 | −700 V | −20 V | −705 V | −50 V |
| 2 | 1 | −700 V | −40 V | −715 V | −100 V |
| 3 | 4 | −700 V | −20 V | −705 V | −50 V |
| 4 | 7 | −700 V | −20 V | −705 V | −55 V |
| 5 | 8 | −700 V | −20 V | −710 V | −45 V |
| 6 | 9 | −700 V | −20 V | −710 V | −45 V |
| 7 | 12 | −700 V | −35 V | −710 V | −60 V |
| 8 | 14 | −700 V | −20 V | −710 V | −45 V |
| 9 | 20 | −700 V | −40 V | −720 V | −55 V |
| 10 | 25 | −700 V | −40 V | −720 V | −60 V |
| Comp. | — | −700 V | −55 V | −850 V | −480 V |

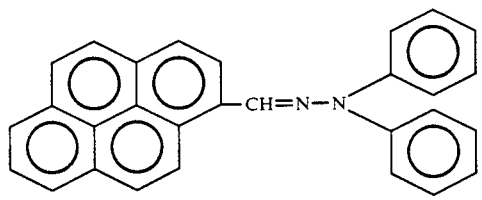

1.5 parts by weight of 4-(2,2'-dicyanovinyl)phenyl 2,4,5-trichlorobenzenesulfonate (compound No. 3) and 100 parts by weight of a polycarbonate resin having the following formula:

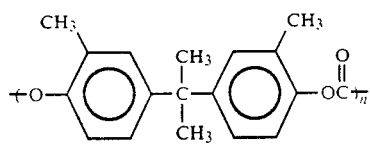

in a mixed solvent of 1,4-dioxane and tetrahydrofuran and thus a charge transfer layer was coated on the charge generation layer and dried at 125° C. for 30 minutes to provide a dried film of 40 μm in thickness.

In this way, a laminated-type electrophotographic photoreceptor was prepared.

EXAMPLES 2 to 10

The procedures in Example 1 were repeated, except that 4-(2,2'-dicyanovinyl)phenyl 2,4,5-trichlorobenzenesulfonate (compound No. 3) was replaced with the other present compounds Nos. 1, 4, 7, 8, 9, 12, 14, 20 and 25.

COMPARATIVE EXAMPLE

The procedure in Example 1 was repeated, except that 4-(2,2'-dicyanovinyl)phenyl 2,4,5-trichlorobenzenesulfonate was omitted.

TEST EXAMPLE

The characteristics of the photoreceptors prepared in Examples 1 to 10 and Comparative Example were tested.

Each photoreceptor was charged at 260 mm/sec (the surface potential at this time was −700 V) followed by exposing and erasing. Then, the dark potential and the residual potential were determined.

Further the above cycle of charging, exposing and erasing was repeated 300,000 times and then the dark potential and the residual potential were determined.

The results are shown in Table 1.

As clear from the results in Table 1, in the electrophotographic photoreceptors comprising the sulfonate ester compounds (I) in the charge transfer layers according to the present invention, the dark potential hardly changed and the accumulation of the residual potential was ignorable after using 300,000 times. On the other hand, in the electrophotographic photoreceptor without the sulfonate ester compound (I), the residual potential was remarkably accumulated. Thus, it can be said that the electrophotographic photoreceptor according to the present invention has the excellent durability.

What is claimed is:

1. An electrophotographic photoreceptor having on a conductive base at least one charge generation layer and at least one charge transfer layer, which comprises a sulfonate ester compound represented by the general formula (I):

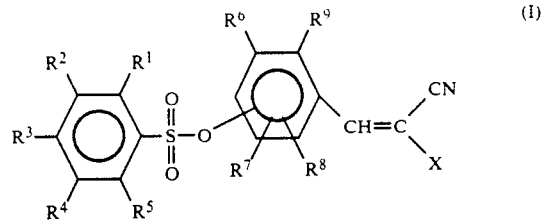

wherein $R^1$, $R^2$, $R^3$, $R^4$ and $R^5$ are independently hydrogen atom, halogen atom, cyano group, nitro group or alkyl group; $R^6$, $R^7$, $R^8$ and $R^9$ are independently hydrogen atom or halogen atom; and X is cyano group, alkoxycarbonyl group, optionally substituted aryloxycarbonyl group or optionally substituted aryl group, in the charge transfer layer.

2. The photoreceptor according to claim 1, wherein the charge transfer layer comprises the sulfonate ester compound, a charge transfer material and a binder resin.

3. The photoreceptor according to claim 2, wherein the amount of the sulfonate ester compound is 0.01 to 30 parts by weight per 100 parts by weight of the binder resin.

4. The photoreceptor according to claim 3, wherein the amount of the sulfonate ester compound is 0.1 to 10 parts by weight per 100 parts by weight of the binder resin.

5. The photoreceptor according to claim 2, wherein the charge transfer material is an electric donative material selected from the group consisting of heterocyclic compounds, aniline derivatives, hydrazone compounds, aromatic amine derivatives, stilbene derivatives and polymers having th above compound in the main chain or the side chain.

6. The photoreceptor according to claim 1, wherein the halogen atom represented by $R^1$ to $R^5$ is chlorine, bromine or iodine.

7. The photoreceptor according to claim 6, wherein the halogen atom is chlorine.

8. The photoreceptor according to claim 1, wherein the alkyl group represented by $R^1$ to $R^5$ is $C_{1-3}$ alkyl.

9. The photoreceptor according to claim 8, wherein the alkyl group is methyl.

10. The photoreceptor according to claim 1, wherein the halogen atom represented by $R^6$ to $R^9$ is chlorine, bromine or iodine.

11. The photoreceptor according to claim 10, wherein the halogen atom is bromine.

12. The photoreceptor according to claim 1, wherein the alkoxycarbonyl group represented by X is methoxycarbonyl, ethoxycarbonyl, propoxycarboyl or butoxycarbonyl.

13. The photoreceptor according to claim 12, wherein the alkoxycarbonyl group is ethoxycarbonyl.

14. The photoreceptor according to claim 1, wherein the optionally substituted aryloxycarbonyl group represented by X is phenoxycarbonyl or naphthyloxycarbonyl which may be substituted with one or more substituents selected from cyano, nitro, alkyl and halogen.

15. The photoreceptor according to claim 14, wherein the optionally substituted aryloxycarbonyl group is phenoxycarbonyl unsubstituted or substituted with chlorine.

16. The photoreceptor according to claim 1, wherein the optionally substituted aryl group represented by X is phenyl or naphthyl which may be substituted with one or more substituents selected from cyano, nitro, alkyl and halogen.

17. The photoreceptor according to claim 16, wherein the optionally substituted aryl group is phenyl unsubstituted or substituted with nitro or cyano.

* * * * *